United States Patent [19]

Acton et al.

[11] 4,353,894

[45] Oct. 12, 1982

[54] 5-IMINODOXORUBICIN

[75] Inventors: Edward M. Acton, Menlo Park; George L. Tong, Cupertino, both of Calif.

[73] Assignee: SRI International, Menlo Park, Calif.

[21] Appl. No.: 317,056

[22] Filed: Nov. 2, 1981

Related U.S. Application Data

[63] Continuation-in-part of Ser. No. 201,522, Oct. 27, 1980, abandoned.

[51] Int. Cl.³ .................... A61K 31/70; C07H 15/24
[52] U.S. Cl. ............................. 424/180; 536/17 A; 536/17 R
[58] Field of Search ............... 536/17 A, 17 R; 534/4; 424/180

[56] References Cited

U.S. PATENT DOCUMENTS 4,109,076  8/1978  Henry et al. ............... 536/17 A
4,181,795  1/1980  Whistler ..................... 536/17 A Primary Examiner—Blondel Hazel
Attorney, Agent, or Firm—Urban H. Faubion; Donovan J. De Witt

[57] ABSTRACT

5-Iminodoxorubicin and its pharmaceutically acceptable acid addition salts having good antitumor activity.

3 Claims, No Drawings

5-IMINODOXORUBICIN

ORIGIN OF INVENTION

This invention described herein was made in the course of work done under a National Cancer Institute Grant No. 1RO1CA257711 from the Department of Health and Human Services.

RELATED APPLICATIONS

This application is a continuation-in-part of application bearing Ser. No. 201,522 filed Oct. 27, 1980 now abandoned.

BACKGROUND OF PRIOR ART

The compound 5-iminodaunorubicin is disclosed in U.S. Pat. No. 4,109,076 issued Aug. 22, 1978 to David W. Henry and George L. Tong.

SUMMARY OF INVENTION

The present invention relates to the novel compound 5-iminodoxorubicin having the structure

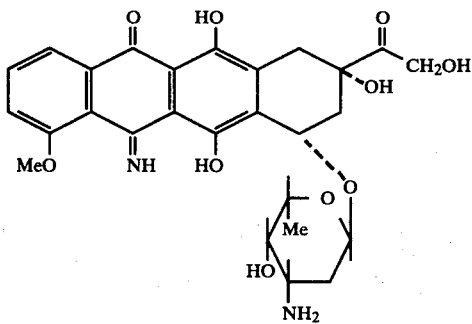

together with its pharmaceutically acceptable acid addition salts as formed with the —NH$_2$ radical of the sugar moiety. The invention also relates to novel pharmaceutical preparations and compositions, sterile in character, containing 5-iminodoxorubicin.

The manner of preparation of 5-iminodoxorubicin and its HCl salt is set forth below in the example. Biological test data showing the good antitumor characteristics of the said compound are also presented below in the table.

The compound of the present invention is preferably employed in salt form since it then has adequate solubility in water. However, said compound can be employed in the non-salt form if so desired. These addition salts are preferably the pharmaceutically acceptable, non-toxic addition salts with suitable inorganic or organic acids such as hydrochloric, hydrobromic, nitric, sulphuric, phosphoric, glycolic, maleic, hydroxymaleic, malic, tartaric, citric, acetic, methanesulphonic and toluene-p-sulphonic acids.

An acid addition salt can be converted into the free compound according to known methods, for example, by treating it with a base, such as an alkali metal or alkaline earth metal hydroxide, for example, lithium hydroxide, sodium hydroxide, potassium hydroxide or calcium hydroxide; with a metal carbonate, such as an alkali metal or an alkaline earth metal carbonate or hydrogen carbonate, for example sodium, potassium or calcium carbonate or hydrogen carbonate; with ammonia; or with a hydroxyl ion exchange resin, or with any other suitable reagent.

An acid addition salt may also be converted into another acid addition salt according to known methods; for example, a salt with an inorganic acid may be treated with a metal salt, for example a sodium, barium or silver salt of an acid in a suitable diluent in which a resulting inorganic salt is insoluble and is thus removed from the reaction medium. An acid addition salt may also be converted into another acid addition salt by treatment with an anion exchange preparation.

The compound of this invention, including the salts thereof, can be administered by any available route, including oral and parenteral (intravenous, intraperitoneal, subcutaneous, and intramuscular) administration. The amount administered is sufficient to ameliorate the leukemia or other type of cancer against which the compounds hereof may prove to be effective. For example, in the treatment of warm-blooded animals, a dosage of a compound of the present invention within the range from about 0.1 mg/kg to about 500 mg/kg per day should be sufficient to ameliorate leukemia. The upper dosage limit is that imposed by toxic side effects and can be determined by trial and error for the animal to be treated.

To facilitate administration, the compound of this invention, including the salts thereof, can be provided in composition form, and preferably in dosage unit form. While any compound selected can be administered per se, it is normally administered in conjunction with a pharmaceutically acceptable carrier therefor, which dilutes the compound and facilitates handling. The term "pharmaceutically acceptable" means that the carrier (as well as the resulting composition) is sterile and non-toxic.

The carrier or diluent can be solid, semisolid, or liquid, and can serve as a vehicle, excipient, or medium for the anti-cancer agent. Exemplary diluents and carriers include lactose, dextrose, sucrose, sorbitol, mannitol, starches, gum acacia, calcium phosphate, mineral oil, cocoa butter, oil of theobroma, alginates, tragacanth, gelatin, syrup, methyl cellulose, polyoxyethylene sorbitan, monolaurate, methyl- and propyl-hydroxybenzoate, talc or magnesium stearate.

For convenience in handling, the compounds hereof and the carrier or diluent can be enclosed or encapsulated in a capsule, sachet, cachet, gelatin, paper or other container, especially when intended for use in dosage units. The dosage units can for example take the form of tablets, capsules, suppositories or cachets.

EXAMPLE

5-Iminodoxorubicin (4), NSC 332988

Background

Quinones occur in the structures of numerous anti-cancer agents and have often become recognized as a key site of biochemical action, particularly in the clinically important anthracyclines doxorubicin (adriamycin 1) and daunorubicin (2). Despite that, 5-iminodaunorubicin (3) is apparently unique as the only quinone-modified analog in the entire anthracycline series. 5-Iminodaunorubicin is of interest because it showed significantly lower cardiotoxicity compared to 1 and 2 in certain tests, yet retained antitumor activity comparable to 1 and 2 in the mouse screen. Analogs with lower cardiotoxicity are widely sought, because this is a cumulative, dose-dependent side effect with 1 and 2 that seriously restricts their use. Other needed improvements are lowered acute toxicity, better efficacy against the unusually broad spectrum of tumors that respond to 1 (in particular) and 2, and activity against tumors that do not respond to 1 or 2.

Although the mechanism of anthracycline cardiotoxicity has not been established and the potential for 3 to show reduced cardiotoxicity allied with antitumor efficacy has not been tested in the clinic, it is tempting to seek a connection between the reduced cardiotoxic effects observed with 3 and its demonstrated reduction in capacity to generate free radicals through cyclic reduction-reoxidation of the quinoid structure. It is clear that other quinone modified anthracyclines should be synthesized and studied.

Preliminary attempts showed that 5-iminodoxorubicin 4 cannot be synthesized directly from 1 by the method for 5-iminodaunorubicin (3), which is obtained in one step by treating 2 with cold methanolic ammonia. Formation of the stable imino derivative exclusively at the 5-position of 3 was attributed to H-bond interactions with the 4-OCH$_3$ and 6-OH groups. Similar treatment of 1 gave extensive decomposition, with only a trace of the desired 4 detectable as a violet spot on thin-layer chromatography (TLC) of the reaction mixture.

The increased lability of doxorubicin (1) relative to 2 is often underestimated. This effect in 1 is largely because of the α-hydroxyketone side chain, which can tautomerize to an α-hydroxyaldehyde, followed by a retro-aldol process, loss of the side chain, and aromatization of the A-ring with elimination of the sugar. Consequently, blocking of the 14-OH is required before a number of common chemical methods, including synthesis of 4, can be applied to 1. In general, availability of efficient methods for blocking the functional groups of 1 is important, but surprisingly there are few detailed procedures for preparing derivatives directly from 1 in satisfactory yield.

Preparative Steps

For synthesis of 4, the 14-O-(MeO)Tr group (14-O-p-anisyldiphenylmethyl) appeared attractive as a base stable group that could be cleaved with mild acid. First of all, however, 1 (the hydrochloride salt) was insoluble in pyridine, the normal (MeO) tritylation solvent, and the suspension underwent essentially no reaction with excess (MeO)TrCl (p-anisyldiphenylmethyl chloride). When 1 was solubilized by adding dimethylformamide (DMF) to the pyridine, tritylation occurred at the sugar NH$_2$ as well as at the 14-OH, as judged by appearance in the TLC of two major spots presumably for the 14-O-(MeO)Tr and the N,14-O-di-(MeO)Tr derivatives. If the pyridine present in the DMF was limited to the equivalent of the HCl to be liberated in the (MeO)tritylation reaction, in order to minimize liberation of the sugar NH$_2$ from the HCl salt and avoid N-(MeO)tritylation, there was considerable glycoside cleavage, presumably acid-catalyzed, after workup. Consequently 1 was first protected by N-trifluoroacetylation. Conversion of 1 in situ to the free base and treatment with S-ethyl trifluorothioacetate afforded N-trifluoroacetyldoxorubicin (5) in 84% yield. Previously, the only direct synthesis of 5 (as opposed to indirectly from 2) was in 40% yield by treating the isolated free base of 1 with trifluoroacetic anhydride and chromatographic purification. A pyridine solution of 5 then underwent (MeO)-tritylation smoothly at room temperature to yield 6 (95%). Amination to give the 5-imino derivative 7 then occurred with ice-cold methanolic ammonia under the conditions for synthesis of 3, except that it was necessary first to dissolve the (MeO)trityl compound 6 in dichloromethane. Conversion to 7 was complete in 26 hours, but was accompanied in small degree (5-10%) by cleavage of the N-trifluoroacetyl blocking group to give 8. Rather than separate 7 and 8 it was efficient to treat the mixture in dioxane-methanol (2:1) with dilute sodium hydroxide at 0° C. to complete the conversion to 8. Chromatographic purification afforded 14-O-(MeO)Tr-5-iminodoxorubicin (8) in 31% yield. Deblocking of the 14-O-(MeO)Tr ether than occurred with 80% acetic acid to give 5-iminodoxorubicin (4) in 81% yield. The overall yield from 1 was 21%.

N-Trifluoroacetyldoxorubicin (5)

To a stirred suspension of 2.98 g (5.14 mmol) of doxorubicin hydrochloride in 100 mL of CHCl$_3$—CH$_3$OH (1:1) cooled in an ice bath was added, dropwise, 10.3 mL of 0.5 M methanolic NaOCH$_3$ followed by 3.3 mL (25.7 mmol) of S-ethyl trifluorothioacetate. The solution was stirred at 23° C. in the dark for 5 hrs; additional 0.5 M methanolic NaOCH$_3$ (1.0 mL) and S-ethyl trifluorothioacetate (0.66 mL, 5.1 mmol) were added and stirring was continued for 17 hrs. After evaporation of the reaction mixture the residue was dissolved in 25 mL of CHCl$_3$—CH$_3$OH (1:1), diluted with 15 mL of toluene and re-evaporated. A solution of the residue in 500 mL of CHCl$_3$—CH$_3$OH (9:1) was washed with 0.1 M citric acid, sodium chloride solution, dried, and evaporated. Trituration of the residue with 40 mL of CH$_2$Cl$_2$ afforded 2.76 g (84%) of N-trifluoroacetyldoxorubicin,[1,2] mp 172°-174°.[1] A sample recrystallized from CHCl$_3$ gave an unchanged mp.

[1]Lit. mp 174°-176°; Arcamone, F.; Franceschi, G; and Penco, S., U.S. Pat. No. 3,803,124.
[2]Arcamone, F.; Barbieri, W.; Franceschi, G.; and Penco, S. Chim. Ind. (Milan) 1969, 51, 834-5.

14-O-p-Anisyldiphenylmethyl-N-trifluoroacetyldoxorubicin (6)

A solution of 2.76 g (4.32 mmol) of N-trifluoroacetyldoxorubicin and 5.35 g (17.3 mmol) of p-anisyldiphenylmethylchloride in 40 mL of dry pyridine was stirred at 23° C. in the dark for 19 hrs. Another 1.33 g (4.3 mmol) of p-anisyldiphenylmethylchloride was added and stirring was continued for 23 hrs. The reaction mixture was diluted with 5 mL of CH$_3$OH, stirred at 23° C. for 1 hr and then poured into 400 mL of cold H$_2$O. The mixture was extracted with CH$_2$Cl$_2$; the combined extracts were washed with NaCl solution, dried, and evaporated. The residue was thrice dissolved in 15 mL of toluene and evaporated. A solution of the gummy residue in 5 mL of CH$_2$Cl$_2$ was stirred and 75 mL of Et$_2$O was added dropwise followed by 75 mL of pet-ether (35°-60°). The resulting precipitate was triturated in the mixture for 1.5 hrs., collected, washed with Et$_2$O-pet-ether (35°-60°) (1:1) and dried to afford 3.75 g (95%) of 14-O-anisyldiphenylmethyl-N-trifluoroacetyldoxorubicin. Homogeneous by TLC on silica gel in CHCl$_3$—CH$_3$OH (19:1), R$_f$ 0.5.

14-O-p-Anisyldiphenylmethyl-5-iminodoxorubicin (8)

To a stirred solution of 300 mL of methanolic ammonia (saturated at 0° C.) in an ice bath was added a solution of 3.73 g (4.09 mmol) of 14-O-p-anisyldiphenylmethyl-N-trifluoroacetyldoxorubicin in 75 mL of CH$_2$Cl$_2$. The cold solution was stirred briefly (1 hr), stored at 0°-5° C. for 26 hrs. and evaporated. The violet residue was twice dissolved in 75 mL of CH$_2$Cl$_2$—CH$_3$OH (9:1) and the solution evaporated. A solution of the residue in 100 mL of $CH_2Cl_2$ was filtered through Celite and evaporated to afford 3.70 g of a mixture of 14-O-p-anisyldiphenylmethyl-5-imino-N-trifluoroacetyldoxorubicin and 14-O-p-anisyldiphenylmethyl-5-iminodoxorubicin. To a stirred solution of the above mixture in 200 mL of dioxane-$CH_3OH$ (2:1) cooled in an ice bath was added 200 mL of 0.2 N NaOH dropwise. After stirring at 0° C. under $N_2$ for 6 hrs the dark blue solution was adjusted to pH 8.0 with 1.0 N AcOH added dropwise. The aqueous mixture was extracted with $CHCl_3$—$CH_3OH$ (19:1); the combined extracts were washed with saturated NaCl, dried, filtered through Celite, and evaporated. The residue (2.82 g) in 15 mL of $CHCl_3$ was chromatographed on a column of silica gel, which was eluted with $CHCl_3$ (200 mL) and then $CHCl_3$—$CH_3OH$ (50:1 to 9:1). After collection of 3.55 L of initial eluate, a 1.05 L fraction was evaporated to yield 1.078 g (31%) of 14-O-p-anisyldiphenylmethyl-5-iminodoxorubicin which was homogeneous by TLC on silica gel in $CHCl_3$—$CH_3OH$ (4:1), $R_f$ 0.3.

5-Iminodoxorubicin Hydrochloride (4)

A solution of 1.073 g (1.32 mmol) of 14-O-p-anisyldiphenylmethyl-5-iminodoxorubicin in 70 mL of 80% AcOH was stirred at 23° C. in the dark for 5 hrs, frozen, and lyophilized. The residue was dissolved in 100 mL of $CHCl_3$—$CH_3OH$ (1:1), the solution was stirred, and 14.3 mL (1.32 mmol) of 0.092 M methanolic hydrogen chloride was added dropwise, followed by 200 mL of $Et_2O$. The resulting precipitate was collected, washed with $CHCl_3$ and with $Et_2O$ to afford 0.642 g (82%) of 5-iminodoxorubicin hydrochloride.

UV-Vis $\lambda_{max}$ ($CH_3OH$) 221 nm ($\epsilon$ 30,200), 233 sh (25,500), 252 (31,600), 305 (7,200), 335 sh (4,500), 360 sh (4,050), 520 sh (8,900), 551 (16,700), 592 (19,600); MS [as the $(Me_3Si)_6$ derivatives] m/e 959 (M—$CH_3$), 944 (M—$2CH_3$). It was homogeneous by TLC on silica gel in $CHCl_3$—$CH_3OH$—2N AcOH (40:10:1) $R_f$ 0.11.

|  | C | H | Cl⁻ | N |
|---|---|---|---|---|
| Anal. Calc. for $C_{27}H_{30}N_2O_{10}$·HCl·$H_2O$ | 54.32 | 5.57 | 5.94 | 4.69 |
| Found | 54.46 | 5.17 | 5.73 | 4.51 |

Structural Diagram of Compounds Utilized in the Above-described Procedure for Preparing 5-Iminodoxorubicin Hydrochloride (4) NSC 332988

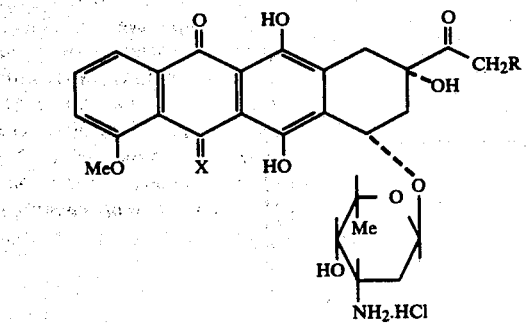

1, R = OH, X = O
2, R = H, X = O
3, R = H, X = NH
4, R = OH, X = NH

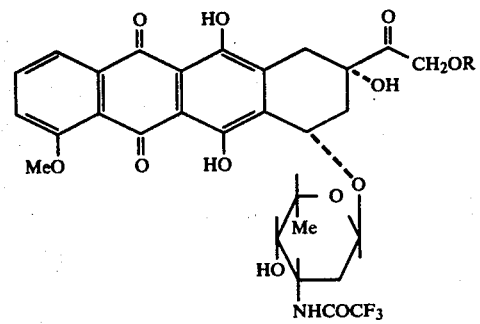

5, R = H

6, R = $\overset{\displaystyle C_6H_5}{\underset{\displaystyle C_6H_5}{C}}$—$C_6H_4$(p-OMe)

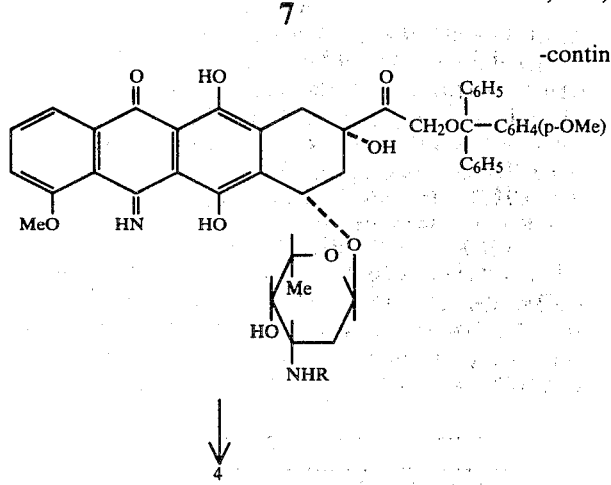

7, R = COCF₃
8, R = H

↓

4

BIOLOGICAL TESTS

Biological testing data for 5-iminodoxorubicin and 5-iminodaunorubicin, as the HCl salt, along with doxorubicin and daunorubicin are presented in the table given below. Such data were obtained when these compounds were tested against lymphocytic leukemia P388 implanted in mice under the auspices of the NCI and according to protocols which use the increased survival time of treated animals compared to controls as the measure of antitumor efficacy.

TABLE

| Compound | NSC[a] # | Activity vs Leukemia P388 in Mice dose schedule q4d 5,9,13[b] | |
|---|---|---|---|
| | | Efficacy in % T/C (survival time of treated/control) | Optimum Dose (mg/kg) |
| 5-Imino-daunorubicin | 254681 | 130 | 3 |
| 5-Imino-doxorubicin | 332988 | 217 | 100 |
| Daunorubicin | 82151 | 130 | 8 |
| Doxorubicin | 123127 | 160 | 8 |

[a]Accession number of the National Cancer Institute.
[b]Ip P388 murine leukemia treated ip on Q4D 5, 9, 13 schedule according to standard NCI protocols. Assay described in R. I. Geran, N. H. Greenberg, M. M. MacDonald, A. M. Schumacker (1972), Protocol 1,200. T/C = ratio of survival time of treated mice to that of untreated controls times 100. Untreated controls survive about 9 days.

We claim:

1. 5-Iminodoxorubicin and its pharmaceutically acceptable acid addition salts.

2. The compound of claim 1 which is 5-iminodoxorubicin hydrochloride.

3. A dosage unit of a pharmaceutical composition for treating leukemia in a warm-blooded animal comprising an amount within a range of from about 0.1 to about 500 mg per dosage unit, therapeutically effective to ameliorate leukemia, of at least one compound selected from the group consisting of 5-iminodoxorubicin and its pharmaceutically acceptable acid addition salts, together with a pharmaceutically acceptable, nontoxic, sterile carrier or diluent therefor.

* * * * *